United States Patent [19]

Hofer et al.

[11] 4,058,603

[45] Nov. 15, 1977

[54] INSECTICIDAL AND ACARICIDAL O-ETHYL-O-[1,6-DIHYDRO-1-SUBSTITUTED-6-OXO-PYRIDAZIN(3)YL]-THIONOBENZENEPHOSPHONIC ACID ESTERS

[75] Inventors: Wolfgang Hofer; Fritz Maurer; Hans-Jochem Riebel, all of Wuppertal; Ingeborg Hammann, Cologne; Wilhelm Stendel, Wuppertal, all of Germany

[73] Assignee: Bayer Aktiengesellschaft, Leverkusen, Germany

[21] Appl. No.: 699,542

[22] Filed: June 24, 1976

[30] Foreign Application Priority Data

July 12, 1975 Germany .............................. 2531340

[51] Int. Cl.² .................. A61K 31/50; C07F 9/65; A01N 9/36
[52] U.S. Cl. ................... 424/200; 260/250 AP
[58] Field of Search ................. 260/250 AP; 424/200

[56] References Cited

U.S. PATENT DOCUMENTS

| | | | |
|---|---|---|---|
| 2,759,937 | 8/1956 | Du Breuil | 260/250 AP |
| 3,310,560 | 3/1967 | Schoenbech et al. | 260/250 AD |
| 3,544,572 | 12/1970 | Fest et al. | 260/250 AP |
| 3,749,720 | 7/1973 | Fest et al. | 260/250 AP |
| 3,867,397 | 2/1975 | Bohner et al. | 424/200 |
| 3,878,210 | 4/1975 | Lorenz et al. | 260/250 AP |
| 3,891,642 | 6/1975 | Lorenz et al. | 260/250 AP |
| B 498,288 | 3/1976 | Hofer et al. | 260/250 AP |

FOREIGN PATENT DOCUMENTS 47-20025  7/1972  Japan .............................. 260/250 AP

OTHER PUBLICATIONS

Schoenbeck et al., II, Chem. Abs. 67, 11497b (1967).
Fest et al. III, Chem. Abs., 72, 100734x (1968).

*Primary Examiner*—Alton D. Rollins
*Assistant Examiner*—Maril L. Berch
*Attorney, Agent, or Firm*—Burgess, Dinklage & Sprung

[57] ABSTRACT

O-Ethyl-O-[1,6-dihydro-1-substituted-6-oxo-pyridazin(-3)yl]-thionobenzenephosphonic acid esters of the formula

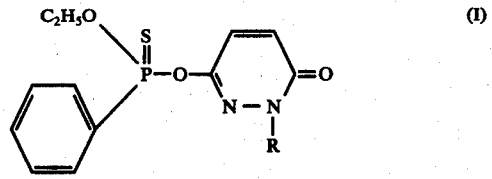

in which
R is alkyl, hydroxyalkyl, halogenoalkyl, cyanoalkyl, carbalkoxyalkyl or carboalkyl, with 1 to 4 carbon atoms in each alkyl radical, phenyl or phenyl substituted by alkyl with 1 to 4 carbon atoms, which possess insecticidal and acaricidal properties.

10 Claims, No Drawings

INSECTICIDAL AND ACARICIDAL O-ETHYL-O-[1,6-DIHYDRO-1-SUBSTITUTED-6-OXO-PYRIDAZIN(3)YL]-THIONOBENZENE-PHOSPHONIC ACID ESTERS

The present invention relates to and has for its objects the provision of particular new 1-substituted O-ethyl-O-[1,6-dihydro-6-oxo-pyridazin(3)yl]-thionobenzenephosphonic acid esters which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from German Published Specification DOS 1,770,067 that certain O-ethyl-O-pyridazinyl-thiobenzenephosphonic acid esters, for example O-ethyl-O-[1,6-dihydro-6-oxo-pyridazin(3)yl]-thionobenzenephosphonic acid ester (Compound A) possess insecticidal and acaricidal properties.

The present invention provides, as new compounds, the O-ethyl-O-pyridazinylthionobenzenephosphonic acid esters of the general formula

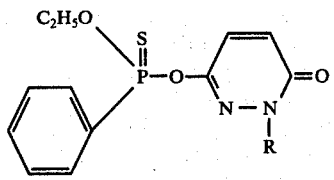

in which
R is alkyl, hydroxyalkyl, halogenoalkyl, cyanoalkyl, carbalkoxyalkyl or carboalkyl, with 1 to 4 carbon atoms in each alkyl radical, phenyl or phenyl substituted by alkyl with 1 to 4 carbon atoms.

Preferably, R represents straight-chain or branched alkyl, hydroxyalkyl, cyanoalkyl or chloroalkyl, in each case with 1 to 3 carbon atoms in the alkyl radical, carbalkoxyalkyl or carboalkyl with 1 or 2 carbon atoms in the alkyl radical, or phenyl which can optionally be monosubstituted or disubstituted by methyl or ethyl.

Surprisingly, the O-ethyl-O-pyridazinylthionobenzenephosphonic acid esters according to the invention exhibit a better insecticidal and acaricidal action than the previously known compound, O-ethyl-O-[1,6-dihydro-6-oxo-pyridazin(3)yl]-thionobenzenephosphonic acid ester, which has an analogous structure and the same type of action. The compounds of the present invention thus represent a genuine enrichment of the art.

The present invention also provides a process for the preparation of an O-ethyl-O-pyridazinylthionobenzenephosphonic acid ester of the formula (I) in which
(a) an O-ethylthionobenzenephosphonic acid ester halide of the general formula

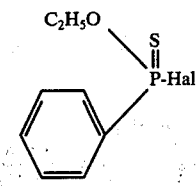

in which
Hal represents halogen, preferably chlorine, is reacted with a 1,6-dihydro-3-hydroxy-6-oxo-pyridazine derivative of the general formula

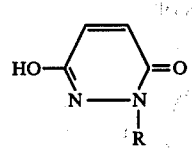

in which
R has the above-mentioned meaning,
if appropriate in the presence of an acid acceptor and, if appropriate, in the presence of a solvent, or
(b) if R denotes hydroxymethyl, O-ethyl-O-[1,6-dihydro-6-oxo-pyridazin(3)yl]-thionobenzenephosphonic acid ester, of the formula

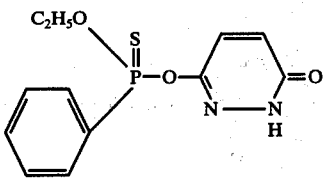

is reacted with formaldehyde (preferably as a formalin solution), or
(c) if R denotes halogenomethyl, O-ethyl-O-[1,6-dihydro-6-oxo-pyridazin(3)yl]-thionobenzenephosphonic acid ester of the formula (IV) is reacted with formaldehyde (preferably as a formalin solution) to give the corresponding N-1-hydroxymethyl compound and the latter is subsequently reacted further, without intermediate isolation, with thionyl chloride, or
(d) if R denotes alkyl, the compound of the formula (IV) is reacted with an alkyl halide of the general formula $$Hal_1\text{-Alkyl} \qquad (V)$$

in which
Alkyl represents alkyl with 1 to 4 carbon atoms, and
$Hal_1$ represents halogen, preferably chlorine or bromine,
if appropriate in the presence of an acid acceptor and, if appropriate, in the presence of a solvent.

If, for example, O-ethyl-thionobenzenephosphonic acid chloride and 1,6-dihydro-1-(2,4-dimethylphenyl)-3-hydroxy-6-oxo-pyridazine or O-ethyl-O-[1,6-dihydro-6-oxo-pyridazin(3)yl]-thionobenzenephosphonic acid ester and formaldehyde or formaldehyde and thionyl chloride or methyl bromide are used as the starting materials, the course of the reaction can be represented by the following formula schemes:

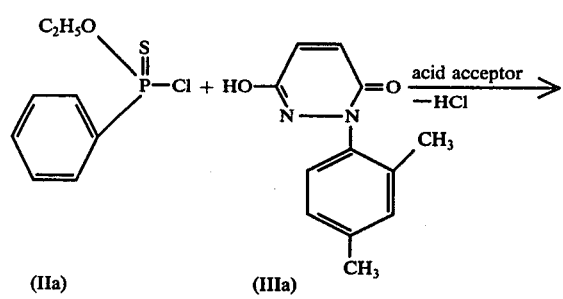

(IIa)  (IIIa)

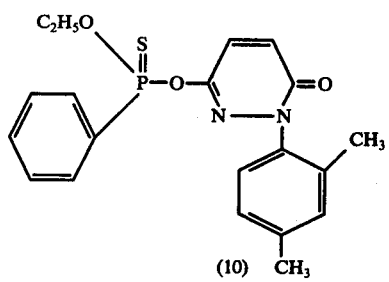

(10)

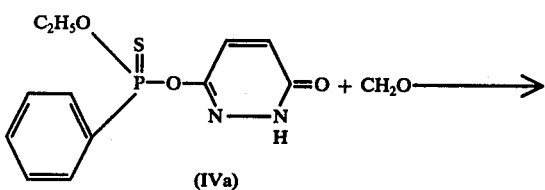

(IVa)

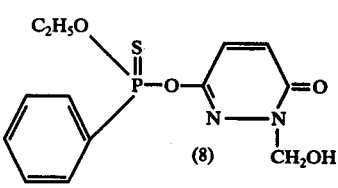

(8)

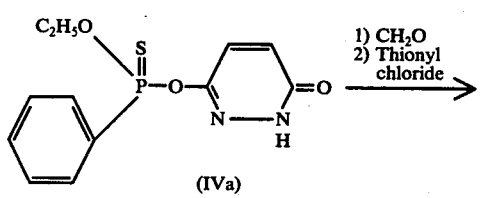

(IVa)

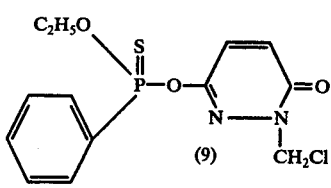

(9)

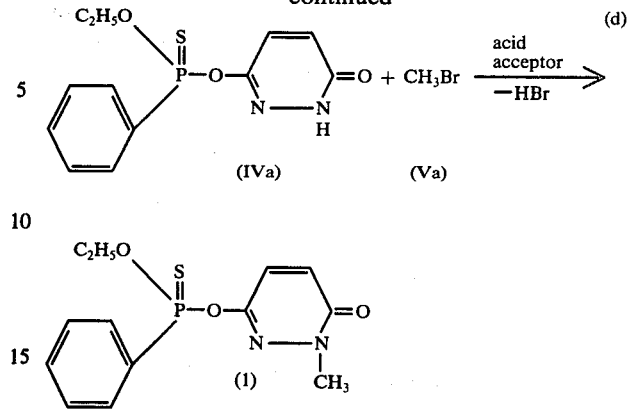

(IVa)  (Va)

(1)

The O-ethylthionobenzenephosphonic acid ester halides (II) to be used as starting materials are known from the literature and can be prepared in accordance with generally customary methods (see, for example, Houben-Weyl "Organische Phosphor-Verbindungen" ("Organic Phosphorus Compounds"), volume XII/1, page 561), as can O-ethyl-O-[1,6-dihydro-6-oxo-pyridazin(-3)yl]-thionobenzenephosphonic acid ester (IV) (see German Published Specification DOS 1,770,067). The alkyl halides (V) are also known compounds. The following may be mentioned as examples: methyl, ethyl, n-propyl and isopropyl chlorides and bromides.

The known 1,6-dihydro-3-hydroxy-6-oxo-pyridazine derivatives (III) can be prepared in accordance with customary methods from appropriately substituted hydrazines and maleic anhydride or from maleic acid hydrazide and vinyl compounds [see, for example, J. Druey, Helv. 37, 510 (1954); K. Eichenberger, H. Staehelin, J. Druey, Helv. 37, 837 (1954); and H. Feuer, R. Harmetz, J. Amer. Chem. Soc. 80, 5877 (1958)].

The following may be mentioned as examples of these: 1-methyl-, 1-ethyl-, 1-n-propyl-, 1-isopropyl-, 1-hydroxymethyl-, 1-(2-hydroxyethyl)-, 1-(3-hydroxypropyl)-, 1-cyanomethyl-, 1-(2-cyanoethyl)-, 1-chloromethyl-, 1-(2-chloroethyl)-, 1-(3-chloropropyl)-, 1-carbomethoxymethyl-, 1-carbethoxymethyl-, 1-carbo-n-propoxymethyl-, 1-carbo-isopropoxymethyl-, 1-(2-carbomethoxyethyl)-, 1-(2-carboethoxyethyl)-, 1-(3-carbomethoxy-propyl)-, 1-(3-carbethoxy-propyl)-, 1-methylcarbomethyl-, 1-ethylcarbomethyl-, 1-(2-methylcarboethyl)-, 1-(2-ethylcarboethyl)-, 1-phenyl-, 1-(2-methylphenyl)-, 1-(2-ethylphenyl)-, 1-(4-methylphenyl)-, 1-(4-ethyl-phenyl)-, 1-(2,4-dimethylphenyl)- and 1-(2,4-diethylphenyl)-1,6-dihydro-3-hydroxy-6-oxo-pyridazines.

Process variants (a) and (d) for the preparation of the compounds according to the invention are preferably carried out in the presence of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

Furthermore, process variants (a) and (d) are preferably carried out in the presence of an acid acceptor.

All customary acid-binding agents can be used as acid acceptors. Alkali metal carbonates and alkali metal alcoholates, such as sodium carbonate, potassium carbonate, sodium methylate and ethylate and potassium methylate and ethylate have proved particularly suitable, as have aliphatic, aromatic or heterocyclic amines, for example triethylamine, trimethylamine, dimethylaniline, dimethylbenzylamine and pyridine.

In all process variants the reaction temperature can be varied within a fairly wide range. In general, the reaction is carried out at between 0° and 150° C, preferably at 40° to 100° C.

In general, the reaction is allowed to take place under normal pressure.

To carry out the process, the reactants are preferably employed in equimolar amounts, since an excess of one or other component produces no significant advantages, except in the case of process variants (b) and (c) wherein the formalin solution is preferably employed in excess. Working up, in all process variants, is preferably effected by cooling the mixture after the reaction has ended, pouring it into an organic solvent, for example methylene chloride, and then working up the organic phase in the usual way by washing, drying and distilling off the solvent.

The new compounds are obtained in the form of oils, which in most cases cannot be distilled without decomposition, but can be freed from the last volatile constituents by so-called "slight distillation", that is to say by prolonged heating under reduced pressure to moderately elevated temperatures, and are purified in this way. They are characterized by the refractive index.

As already mentioned, the O-ethyl-O-pyridazinylthionobenzenephosphonic acid esters according to the invention are distinguished by an excellent insecticidal and acaricidal activity. They are not only active against plant pests, pests harmful to health and pests of stored products, but also, in the veterinary medicine field, against animal parasites (ectoparasites), such as parasitic fly larvae. They have a low phytotoxicity and a good action against both sucking and biting insects and against mites.

For this reason, the compounds according to the invention can be employed successfully as pesticides in plant protection and in the hygiene field, the field of protection of stored products and the veterinary field.

To the sucking insects there belong, in the main, aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis,* and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus.*

In the case of the biting insects, above all there should be mentioned butterfly and moth caterpillars (*Lepidoptera*) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (*Coleoptera*), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The *Diptera* comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (*Acarina*) there are classed, in particular, the spider mites (*Tetranychidae*) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and-/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other nematocides, insecticides, acaricides and fungicides, or bactericides, rodenticides, herbicides, fertilizers, growth-regulating agents, etc., if desired, or in the form of particular dosage preparations for specific application made therefrom, such as solution, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of form 50–100 microns, or even less, i.e. mist form, for example by airplane crop spraying techniques. Only up to at most about a few liters/hectare are needed, and often amounts only up to about 15 to 1,000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

*Phaedon* larvae test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all of the beetle larvae had been killed whereas 0% means that none of the beetle larvae had been killed.

The active compounds, the concentrations of the active compounds, the evaluation times and the results can be seen from the following table:

Table 1

(*Phaedon* larvae test)

| Active compound | Active compound concentration in % | Degree of destruction in % after 3 days |
|---|---|---|
| 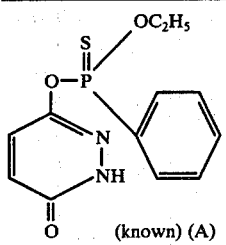 (known) (A) | 0.01<br>0.001 | 100<br>0 |
| 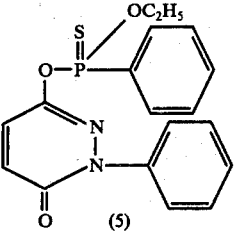 (5) | 0.01<br>0.001 | 100<br>100 |

EXAMPLE 2

*Myzus* test (contact action)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all of the aphids were killed whereas 0% means that none of the aphids were killed.

The active compounds, the concentrations of the active compounds, the evaluation times and the results can be seen from the following table:

Table 2

(*Myzus* test)

| Active compound | Active compound concentration in % | Degree of destruction in % after 1 day |
|---|---|---|
| 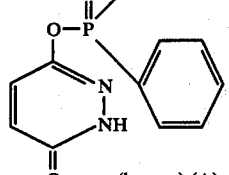 (known) (A) | 0.1<br>0.01 | 80<br>0 |
| 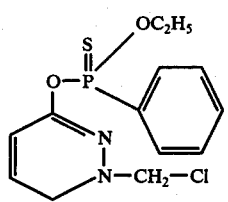 (9) | 0.1<br>0.01 | 100<br>100 |
| 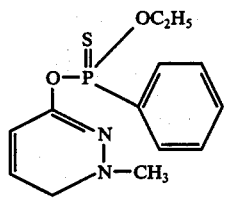 (1) | 0.1<br>0.01 | 100<br>100 |
| 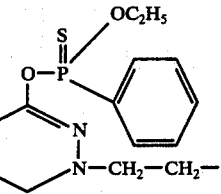 (3) | 0.1<br>0.01 | 100<br>100 |
| 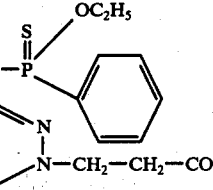 (4) | 0.1<br>0.01 | 100<br>98 |

EXAMPLE 3

*Tetranychus* test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet.

11

These bean plants were heavily infested with the two-spotted spider mite (*Tetranychus urticae*) in all stages of development.

After the specified periods of time, the degree of destruction was determined as a percentage: 100% means that all of the spider mites were killed whereas 0% means that none of the spider mites were killed.

The active compounds, the concentrations of the active compounds, the evaluation times and the results can be seen from the following table:

Table 3

(*Tetranychus* test)

| Active compound | Active compound concentration in % | Degree of destruction in % after 1 day |
|---|---|---|
| ![structure] OC₂H₅ / S=P / O-P / N-NH / O (known) (A) | 0.1 | 0 |
| ![structure] OC₂H₅ / S=P / O-P / N-N-CH₃ / O (1) | 0.1 | 90 |
| ![structure] OC₂H₅ / S=P / O-P / N-N-CH₂-CH₂-CN / O (3) | 0.1 | 90 |

EXAMPLE 4

Test with parasitic fly larvae (*Lucilia cuprina*)
Solvent: 35 parts by weight of ethylene polyglycol monomethyl ether
Emulsifier: 35 parts by weight of nonylphenyl polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approx. 2 cm³ of horse muscle. 0.5 ml of the preparation of active compound was applied to this horse meat. After 24 hours, the degree of destruction in % was determined. 100% means that all of the larvae had been killed and 0% means that no larvae had been killed.

12

The active compounds investigated, the concentrations of the active compounds used and the results obtained can be seen from the table which follows:

Table 4

(Test with parasitic fly larvae/*Lucilia cuprina*)

| Active compound | Active compound concentration in ppm | Degree of destruction in % |
|---|---|---|
| ![structure] OC₂H₅ / S=P / O-P / N-NH / O (known) (A) | 300 | 0 |
| ![structure] OC₂H₅ / S=P / O-P / N-N-⟨⟩-CH₃ / O (7) | 100 10 | 100 100 |
| ![structure] OC₂H₅ / S=P / O-P / N-N-⟨⟩ / O (5) | 100 10 | 100 >50 |

The process of the present invention is illustrated by the following preparative Examples.

EXAMPLE 5

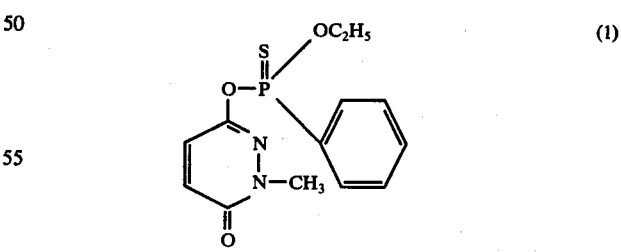

(1)

33 g (0.15 mole) of O-ethyl-benzenethionophosphonic acid ester chloride were added dropwise to a suspension of 18.9 g (0.15 mole) of 1,6-dihydro-3-hydroxy-1-methyl-6-oxo-pyridazine and 21.4 g (0.155 mole) of potassium carbonate in 200 ml of acetonitrile. The mixture was warmed to 40° C for 3 hours, the solid was filtered off and the filtrate was poured into 200 ml of toluene. The toluene solution was washed with saturated sodium bicarbonate solution and water, dried over sodium sulfate and then concentrated. In this way, 35 g (71% of theory) of O-ethyl-O-[1,6-dihydro-1-methyl-6-oxo-pyridazin(3)yl]-thionobenzenephosphonic acid ester were obtained in the form of a brown oil having a refractive index $n_D^{22}$ of 1.5865.

The following compounds of the formula (I)

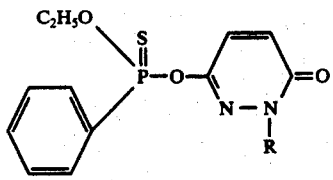

(I)

could be prepared analogously:

| Compound No. | R | Yield (% of theory) | Physical data (refractive index) |
|---|---|---|---|
| 2 | —CH₂—CH₂—CO—CH₃ | 61 | $n_D^{22}$:1,5770 |
| 3 | —CH₂—CH₂—CN | 63 | $n_D^{22}$:1,5747 |
| 4 | —CH₂—CH₂—CO—OCH₃ | 60 | $n_D^{22}$:1,5678 |
| 5 | —CH₂—C₆H₅ | 74 | $n_D^{22}$:1,6199 |
| 6 | —CH₂—CH₂—OH | 63 | $n_D^{22}$:1,5905 |
| 7 | —CH₂—C₆H₄—CH₃ | 65 | $n_D^{22}$:1,6078 |

EXAMPLE 6

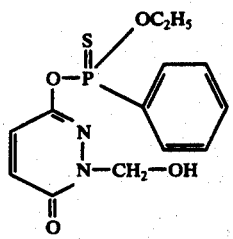

A mixture of 29.6 g (0.1 mole) of O-ethyl-O-[1,6-dihydro-6-oxo-pyridazin(3)yl]-thionobenzenephosphonic acid ester and 50 ml of a 30% strength formalin solution was heated to 100° C for 10 minutes. The reaction mixture was then cooled and extracted with methylene chloride and the organic phase was dried over sodium sulfate and then concentrated. In this way, 23 g (71% of theory) of O-ethyl-O-[1,6-dihydro-1-hydroxymethyl-6-oxo-pyridazin(3)yl]-thionobenzenephosphonic acid ester were obtained in the form of a yellow oil having a refractive index $n_D^{23}$ of 1.5232.

EXAMPLE 7

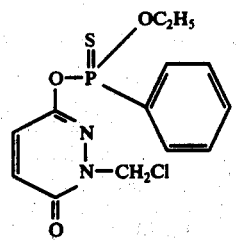

(9)

A mixture of 29.6 g (0.1 mole) of O-ethyl-O-[1,6-dihydro-6-oxo-pyridazin(3)yl]-thionobenzenephosphonic acid ester and 50 ml of 30% strength formalin solution was heated to 100° C for 10 minutes. The reaction mixture was then cooled and extracted twice with a total of 200 ml of carbon tetrachloride. 13.5 g (0.1 mole) of thionyl chloride were added dropwise to the carbon tetrachloride solution. The batch was subsequently warmed for 2 hours to 70° C and then cooled, washed with saturated sodium bicarbonate solution and water and dried over sodium sulfate. After stripping off the solvent, 22 g (64% of theory) of O-ethyl-O-[1,6-dihydro-1-chloromethyl-6-oxo-pyridazin(3)yl]-thionobenzenephosphonic acid ester were obtained in the form of a yellow oil having a refractive index $n_D^{20}$ of 1.5432.

It will be appreciated that the instant specification and examples are set forth by way of illustration and not limitation, and that various modifications and changes may be made without departing from the spirit and scope of the present invention.

What we claim is:

1. An O-ethyl-O-[1,6-dihydro-1-substituted-6-oxo-pyridazin(3)yl]-thionobenzenephosphonic acid ester of the formula

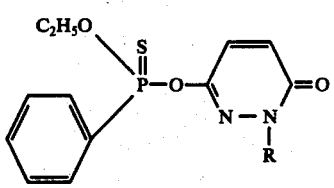

(8)

in which
R is alkyl, hydroxyalkyl, halogenoalkyl, cyanoalkyl, carbalkoxyalkyl or carboalkyl, with 1 to 4 carbon atoms in each alkyl radical, phenyl or phenyl substituted by alkyl with 1 to 4 carbon atoms.

2. A compound according to claim 1, in which R is alkyl, hydroxyalkyl, cyanoalkyl or chloroalkyl with 1 to 3 carbon atoms in each alkyl radical, carbalkoxyalkyl or carboalkyl with 1 or 2 carbon atoms in each alkyl radical, phenyl, or phenyl monosubstituted or disubstituted by methyl or ethyl.

3. The compound according to claim 1 wherein such compound is O-ethyl-O-[1,6-dihydro-1-methyl-6-oxo-pyridazin(3)yl]-thionobenzenephosphonic acid ester of the formula

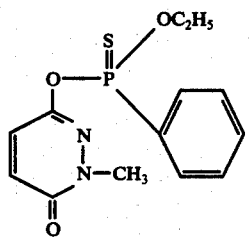

4. The compound according to claim 1 wherein such compound is O-ethyl-O-[1,6-dihydro-1-(2-cyanoethyl)-6-oxo-pyridazin(3)yl]-thionobenzenephosphonic acid ester of the formula 5. The compound according to claim 1 wherein such compound is O-ethyl-O-[1,6-dihydro-1-(2-carbomethoxy-ethyl)-6-oxo-pyridazin(3)yl]-thionobenzenephosphonic acid ester of the formula

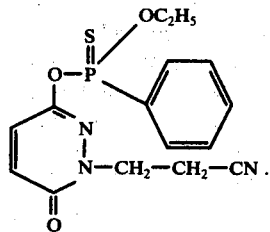

6. The compound according to claim 1 wherein such compound is O-ethyl-O-[1,6-dihydro-1-phenyl-6-oxo-pyridazin(3)yl]-thionobenzenephosphonic acid ester of the formula

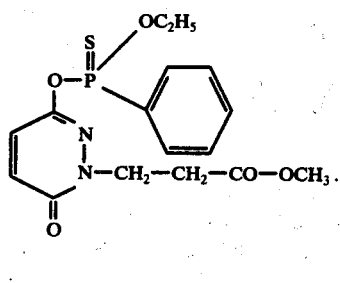

7. The compound according to claim 1 wherein such compound is O-ethyl-O-[1,6-dihydro-1-chloromethyl-6-oxo-pyridazin(3)yl]-thionobenzenephosphonic acid ester of the formula

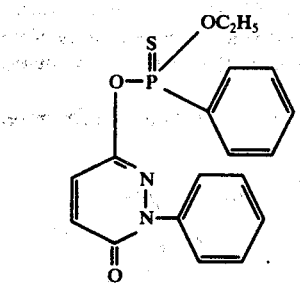

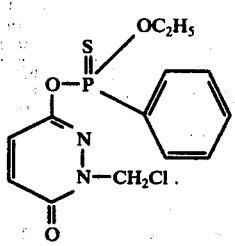

8. An insecticidal or acaricidal composition containing as active ingredient an insecticidally or acaricidally effective amount of a compound according to claim 1 in admixture with a conventional pesticide diluent.

9. A method of combating insects or acarids which comprises applying to the insects or acarids or to a habitat thereof an insecticidally or acaricidally effective amount of a compound according to claim 1.

10. The method according to claim 9, wherein such compound is
O-ethyl-O-[1,6-dihydro-1-methyl-6-oxo-pyridazin(-3)yl]-thionobenzenephosphonic acid ester,
O-ethyl-O-[1,6-dihydro-1-(2-cyanoethyl)-6-oxo-pyridazin(3)yl]-thionobenzenephosphonic acid ester,
O-ethyl-O-[1,6-dihydro-1-(2-carbomethoxy-ethyl)-6-oxo-pyridazin(3)yl]-thionobenzenephosphonic acid ester,
O-ethyl-O-[1,6-dihydro-1-phenyl-6-oxo-pyridazin(-3)yl]-thionobenzenephosphonic acid ester, or
O-ethyl-O-[1,6-dihydro-1-chloromethyl-6-oxo-pyridazin(3)yl]-thionobenzenephosphonic acid ester.